(12) United States Patent
Kim et al.

(10) Patent No.: US 10,575,798 B2
(45) Date of Patent: Mar. 3, 2020

(54) X-RAY DETECTING APPARATUS (71) Applicant: SAMSUNG ELECTRONICS CO., LTD., Suwon-si (KR)

(72) Inventors: Young Ik Kim, Suwon-si (KR); Jin Woo Park, Osan-si (KR); Hyung Jin Ham, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/504,737

(22) PCT Filed: Jul. 28, 2015

(86) PCT No.: PCT/KR2015/007864
§ 371 (c)(1),
(2) Date: Feb. 17, 2017

(87) PCT Pub. No.: WO2016/028003
PCT Pub. Date: Feb. 25, 2016

(65) Prior Publication Data
US 2017/0258422 A1  Sep. 14, 2017

(30) Foreign Application Priority Data

Aug. 20, 2014  (KR) .......................... 10-2014-0108249

(51) Int. Cl.
*A61B 6/00*     (2006.01)
*A61B 6/04*     (2006.01)

(52) U.S. Cl.
CPC .......... *A61B 6/4208* (2013.01); *A61B 6/0407* (2013.01); *A61B 6/4283* (2013.01); *A61B 6/4452* (2013.01); *A61B 6/4464* (2013.01)

(58) Field of Classification Search
CPC ....... A61B 6/44; A61B 6/4283; A61B 6/4429; A61B 6/102; G01T 1/244
See application file for complete search history.

(56) References Cited

U.S. PATENT DOCUMENTS 5,464,984 A  *  11/1995  Cox .................... G01T 1/2018
                                                    250/370.11
5,798,558 A  *  8/1998   Tyson ................. H01L 25/0655
                                                    257/444
(Continued)

FOREIGN PATENT DOCUMENTS

JP        2011-128172 A    6/2011
JP         2012-73186 A    4/2012
WO       2013/190408 A1   12/2013

OTHER PUBLICATIONS

International Search Report, issued by International Searching Authority in corresponding International Application No. PCT/KR2015/007864, dated Nov. 25, 2015, (PCT/ISA/210).

(Continued)

*Primary Examiner* — Kenneth J Malkowski
(74) *Attorney, Agent, or Firm* — Sughrue Mion, PLLC (57) ABSTRACT

An x-ray detecting apparatus having a housing, a detecting panel provided at an inside the housing as to detect x-rays, and a circuit board having a first surface thereof bordering with the detecting panel and a second surface thereof provided with at least one electronic component installed thereto is provided.

19 Claims, 6 Drawing Sheets

(56) References Cited

U.S. PATENT DOCUMENTS

| | | | | |
|---|---|---|---|---|
| 2002/0191828 A1* | 12/2002 | Colbeth | ............... | H04N 5/32 |
| | | | | 382/132 |
| 2009/0065703 A1* | 3/2009 | Jadrich | ............. | G01T 1/2928 |
| | | | | 250/370.11 |
| 2009/0202044 A1 | 8/2009 | Wu et al. | | |
| 2012/0292515 A1* | 11/2012 | Zhang | ................... | G01T 7/00 |
| | | | | 250/361 R |
| 2013/0043400 A1* | 2/2013 | Nakatsugawa | ...... | A61B 6/4283 |
| | | | | 250/366 |
| 2015/0131785 A1* | 5/2015 | Topfer | ............. | A61B 6/4233 |
| | | | | 378/98 |

OTHER PUBLICATIONS

Written Opinion, issued by International Searching Authority in corresponding International Application No. PCT/KR2015/007864, dated Nov. 25, 2015, (PCT/ISA/237).

* cited by examiner

X-RAY DETECTING APPARATUS

TECHNICAL FIELD

Disclosed is an x-ray detecting apparatus provided to detect x-rays.

BACKGROUND ART

An x-ray imaging system 1, for example, a CT (Computed Tomography) or a breast imaging apparatus, is an imaging system to obtain images with respect to an inside a subject by radiating x-rays, in other words, Roentgen rays, at the subject such as a human body or an object, and uses the nature of the x-rays absorbed or penetrated depending on the characteristics of the objects through which the x-rays pass through when the x-rays are radiated at the subject. The x-ray imaging apparatus as the above is used as to detect abnormality such as lesion at an inside a human body or to determine an inside structure of an object or a component, or is used as to scan baggage at an airport, etc.

The x-ray imaging system 1 includes an x-ray detecting apparatus to detect x-rays and output electrical signals that correspond to the detected x-rays.

DISCLOSURE OF INVENTION

Technical Problem

The present invention provides an x-ray detecting apparatus having an efficient inside structure.

Solution to Problem

According to an aspect of the present invention, there is provided an x-ray detecting apparatus including: a housing; a detecting panel provided at an inside the housing as to detect x-rays; and a circuit board having a first surface thereof making contact with the detecting panel and a second surface thereof provided with at least one electronic component installed thereto.

Also, there is the x-ray detecting apparatus further including: a supporting member provided at the second surface of the circuit board as to support the circuit board.

Also, there is the supporting member including: at least one accommodation unit at which a device installed at the circuit board is accommodated.

At this time, the supporting member may be formed along borders of the circuit board.

Also, the supporting member may be formed in a lattice structure or a honeycomb structure.

Meanwhile, there is the x-ray detecting apparatus further including: a buffering unit provided between the detecting panel and the circuit board.

Also, there is the circuit board further including: a shielding layer as to shield x-rays.

Also, the circuit board and the detecting panel may be bonded to each other.

Also, the circuit board and the supporting member may be bonded to each other.

Also, there is the x-ray detecting apparatus further including: a protective layer provided between the detecting apparatus and the housing as to absorb outside impact.

According to another aspect of the present invention, there is provided an x-ray detecting apparatus including: a circuit board having a first surface provided with at least one electrical component installed thereto; a detecting panel provided while making contact with a second surface of the circuit board; and a supporting member provided at the first surface of the circuit board as to fix the circuit board.

At this time, the detecting panel may be fixed by the circuit board while bonded at the circuit board.

Also, the circuit board may be bonded to the supporting member.

Also, there is provided the supporting member further including: an accommodation unit to accommodate electrical components.

Also, the supporting member may be provided along the borders of the circuit board, and the accommodation unit may be formed at the center of the supporting member.

Also, the accommodation unit may be formed in a lattice structure.

Also, the accommodation unit may be formed in a honeycomb structure.

Also, there is provided the circuit board further including: a shielding layer to shield x-rays.

Advantageous Effects OF Invention

According to the above-described aspects of the present invention, since the detecting panel and the circuit board are bordered each other, the circuit panel may be integrally formed, and therefore, the space for the installation of the circuits may be maximized.

Also, since the detecting panel is supported by the circuit board, no separate member is needed to be added to support the detecting panel.

MODE FOR THE INVENTION

The advantages and characteristics of the present invention and the methods of accomplishing such will be clarified by referring to the embodiments that are to be described below along with the attached drawings. However, the present invention is not limited to the embodiments shown hereinafter, and may be implemented in various shapes that are different to each other, while the embodiments are provided in order to fully describe the present invention and to inform those skilled in the art of the full scope of the invention, and the present invention may only be defined without departing from the principles and aspect of the present invention, the scope of which is defined in the claims and their equivalents.

The terminologies used in the present invention are selected that are presently used in general, while considering the functions of the present invention. However, the terminologies as such may be changed according to the intentions of those skilled in the art or precedents, or introductions of new technologies. Also, in certain cases, the terminologies that are voluntarily selected by the applicant of the present intention may be present, and in the cases as such, the definitions of the terminologies as such will be described in the section provided for descriptions of such. Therefore, the terminologies used in the present disclosure will be defined on the basis of the entire contents of the present invention, as well as on the basis of the definitions that the terminologies are provided with.

When describing a case of a certain portion "including" a certain component, such is referred to the fact that, unless otherwise specified, other components are further included along with the certain component without the other components being excluded. Also, terminologies such as "portion," "module," and "unit" each is referred to a single unit provided to process at least a single function or motion, and may be implemented as hardware components such as software, FPGA, or ASIC, or may be implemented by coupling of software and hardware. However, the terminologies such as "portion," "module," and "unit" are not limited to the software or the hardware. The terminologies such as "portion," "module," and "unit" may be composed to be present at a storage medium capable of addressing, or may be composed to regenerate at least one processor. Therefore, as one example, the terminologies such as "portion," "module," and "unit" include software components, activeX software components, class components, task components, processes, functions, procedures, sub-routines, segments of program codes, drivers, firmware, micro codes, circuits, data, database, data structures, arrays, and variables.

The invention is described more fully hereinafter with reference to the accompanying drawings, in which exemplary embodiments of the invention are shown.

Figure 1:
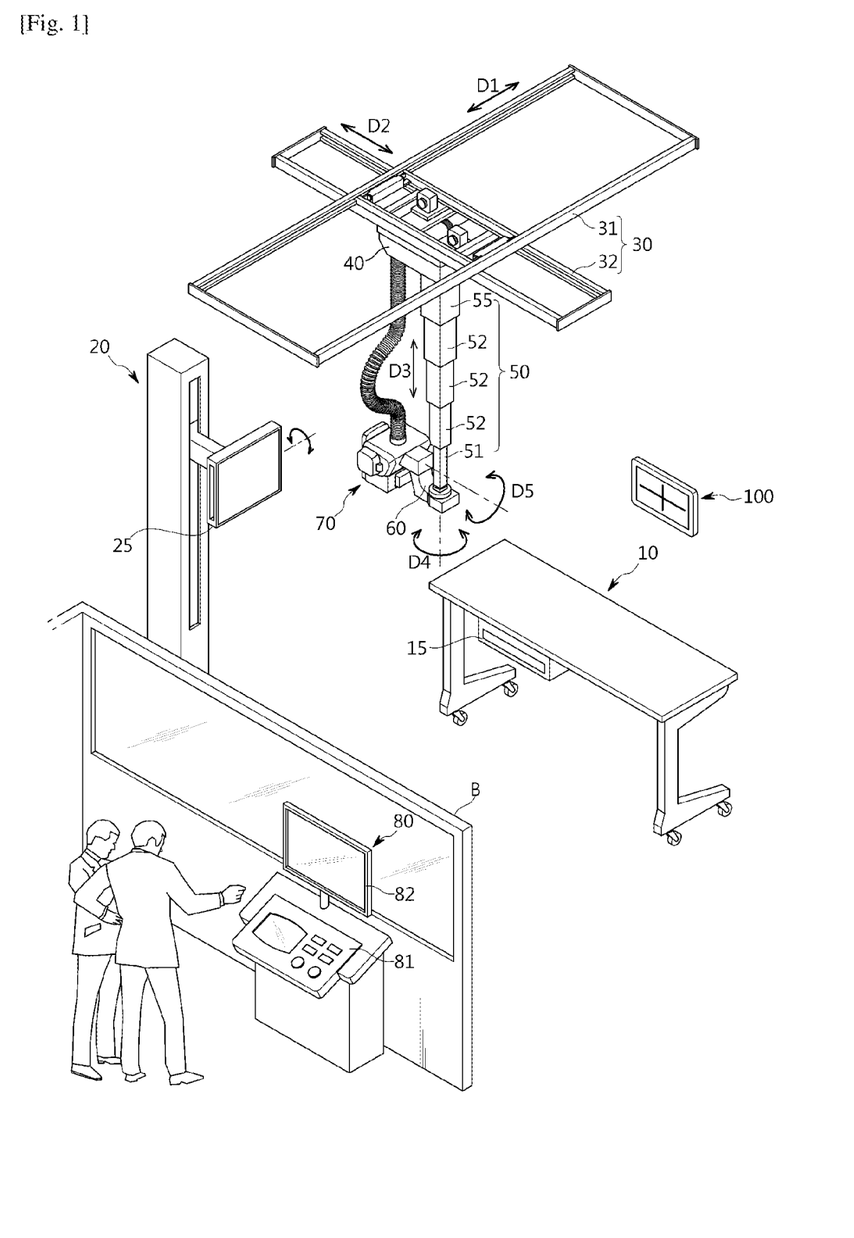
FIG. 1 is a drawing illustrating one example of an x-ray imaging system provided with an x-ray detecting apparatus according to one embodiment.
Figure 2:
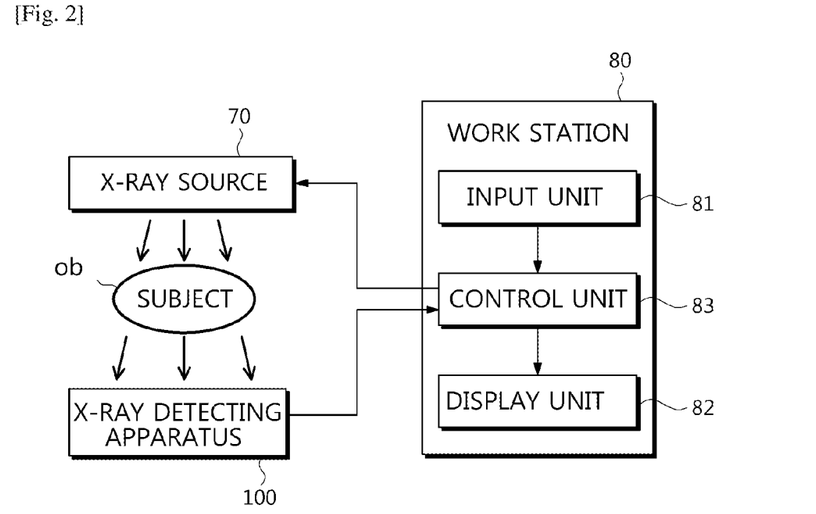
FIG. 2 is a control block diagram for explaining the x-ray imaging system provided with the x-ray detecting apparatus according to one embodiment.
Figure 3:
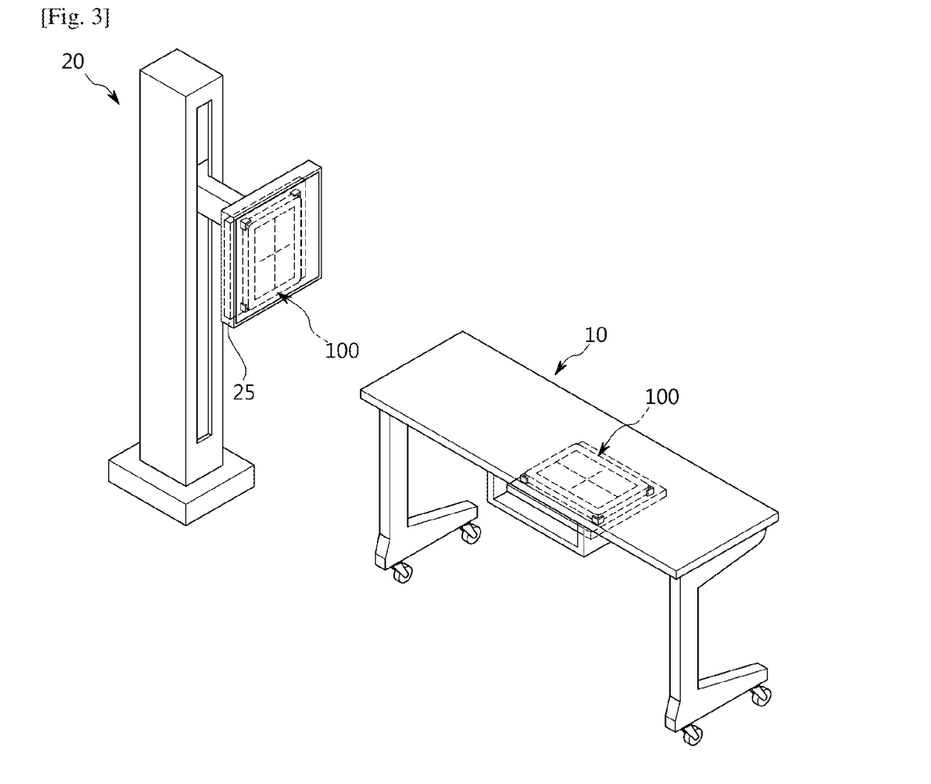
FIG. 3 is a drawing for explaining an example of usage of the x-ray detecting apparatus according to one embodiment.

FIG. 1 is a drawing illustrating one example of an x-ray imaging system provided with an x-ray detecting apparatus according to one embodiment, FIG. 2 is a control block diagram for explaining the x-ray imaging system provided with the x-ray detecting apparatus according to one embodiment, and FIG. 3 is a drawing for explaining an example of usage of the x-ray detecting apparatus according to one embodiment.

Referring to FIG. 1 to FIG. 3, the x-ray imaging system 1 may include a guide rail 30, a moving carriage 40, a post frame 50, a rotating joint 60, an x-ray source 70, and a work station 80. The x-ray imaging system 1 may further include an imaging table 10 and an imaging stand 20 at which an x-ray detecting apparatus 100 may be installed.

The guide rail 30, the moving carriage 40, and the post frame 50 are provided as to move the x-ray source 70 toward a subject.

The guide rail 30 includes a first guide rail 31 and a second guide rail 32 installed as to form a predetermined angle with respect to each other. The first guide rail 31 and the second guide rail 32 are preferred to be extended toward directions that perpendicularly cross with respect to each other.

The first guide rail 31 is installed at a ceiling of a test room in which an x-ray imaging apparatus is disposed.

The second guide rail 32 is positioned at a lower side of the first guide rail 31, and is slidingly mounted at the first guide rail 31. A first direction D1 is defined toward a direction to which the first guide rail 31 is extended, and a second direction D2 is defined toward a direction to which the second guide rail 32 is extended. Therefore, the first direction D1 and the second direction D2 are crossed perpendicularly, and may be parallel with respect to the ceiling of the test room.

The moving carriage 40 is disposed at a lower side of the second guide rail 32 as to be moved along the second guide rail 32. A roller (not shown) provided as to move along the second guide rail 32 may be installed at the moving carriage 40. Therefore, the moving carriage 40 may be moved toward the first direction D1 together with the second guide rail 32, and may be moved toward the second direction D2 along the second guide rail 32. The post frame 50 is positioned at a lower side of the moving carriage 40 while fixed at the moving carriage 40. The post frame 50 may be provided with a plurality of post frames 51, 52, 53, 54, and 55.

The plurality of post frames 51, 52, 53, 54, and 55 each is connected with respect to each other as to be foldedly hinged, so that the length of the post frame 50 may be increased or decreased toward vertical directions of the test room while fixed at the moving carriage 40.

A third direction D3 is defined toward a direction to which the length of the post frame 50 is increased or decreased. Therefore, the third direction D3 may cross perpendicularly with respect to the first direction D1 and the second direction D2.

The x-ray source 70 is an apparatus provided to radiate x-rays at a subject. Here, the subject may be a body of a human being or animal, but is not limited hereto, and the subject may be referred to any object whose inside structure can be displayed as an image by the x-ray imaging system 1.

The rotating joint 60 is disposed between the x-ray source 70 and the post frame 50. The rotating joint 60 couples the x-ray source 70 into the post frame 50, and supports the weight that is applied at the x-ray source 70.

The rotating joint 60 is provided so that the x-ray source 70 is rotated while having a central axis of the post frame 50, which is extended toward vertical directions of the test room, as a center. Therefore, the x-ray source 70 may be rotated toward a fourth direction D4 on a plane surface that is perpendicularly formed with respect to the third direction D3.

Also, the rotating joint 60 is provided so that the x-ray source 70 is rotated on a plane surface that is perpendicularly formed with respect to the ceiling of the test room. Therefore, the x-ray source 70 may be rotated toward a fifth direction D5 on a plane surface that is parallelly formed with respect to the first direction D1 or the second direction D2.

The x-ray detecting apparatus 100 detects x-rays that penetrated through a subject, and outputs electrical signals that correspond to the detected x-rays. Hereinafter, the electrical signals that are output from the x-ray detecting apparatus 100 are referred to as x-ray data. With respect to the x-ray detecting apparatus 100, detailed descriptions will be provided below.

A Printed Circuit Board (PCB) 130 having various processing apparatuses such as a Central Processing Unit (CPU)

and a Graphic Processing Unit (GPU) and various types of storage apparatuses may be installed at the work station 80.

A shielding layer B is provided in between the work station 80 and the test room as to shield x-rays, so that even during the time when x-ray imaging is in progress, a user may be able to input information or manipulate apparatuses through the shielding layer B in a state of not being exposed to the x-rays.

In particular, the work station 80 may include an input unit 81, a display unit 82, and a control unit 83.

The input unit 81 may include at least one of a switch, a keyboard, a trackball, a mouse, and a touch screen, and in a case when the input unit 81 is implemented in the form of software such as a GUI (Graphic User Interface), the input unit 81 may be displayed through the display unit 82.

The display unit 82 displays information to control the x-ray imaging system 1, or displays x-ray images. The display unit 82 may be implemented in the form of a Cathod Ray Thbe (CRT), a Liquid Crystal Display (LCD), or a Light Emitting Diode (LED), but is not limited hereto.

The control unit 83 controls the x-ray imaging system in general. In particular, the control unit 83 may be able to control the x-ray source 70 so that x-rays are radiated at a subject according to the imaging conditions, and may be able to generate x-ray images on the basis of the x-ray data from that are received from the x-ray detecting apparatus 100.

Referring to FIG. 3, the x-ray detecting apparatus 100 may be mounted at the imaging table 10 or the imaging stand 20 according to the position of x-ray imaging. Mounting units 15 and 25 are provided at the imaging table 10 and the imaging stand 20, respectively, so that the x-ray detecting apparatus 100 is mounted.

That is, a user mounts the x-ray detecting apparatus 100 according to the position of x-ray imaging of a subject, and then proceeds with the x-ray imaging by moving the x-ray source 70 so that the x-rays are radiated at the position at which the x-ray detecting apparatus 100 is mounted.

The x-ray detecting apparatus 100 as such is to be provided with the size having a thickness according to a predetermined standard, for example, within about 15, and is preferred to be lightweight to be easily moved. Hereinafter, the x-ray detecting apparatus 100 according to one embodiment will be described in detail.

Figure 4:
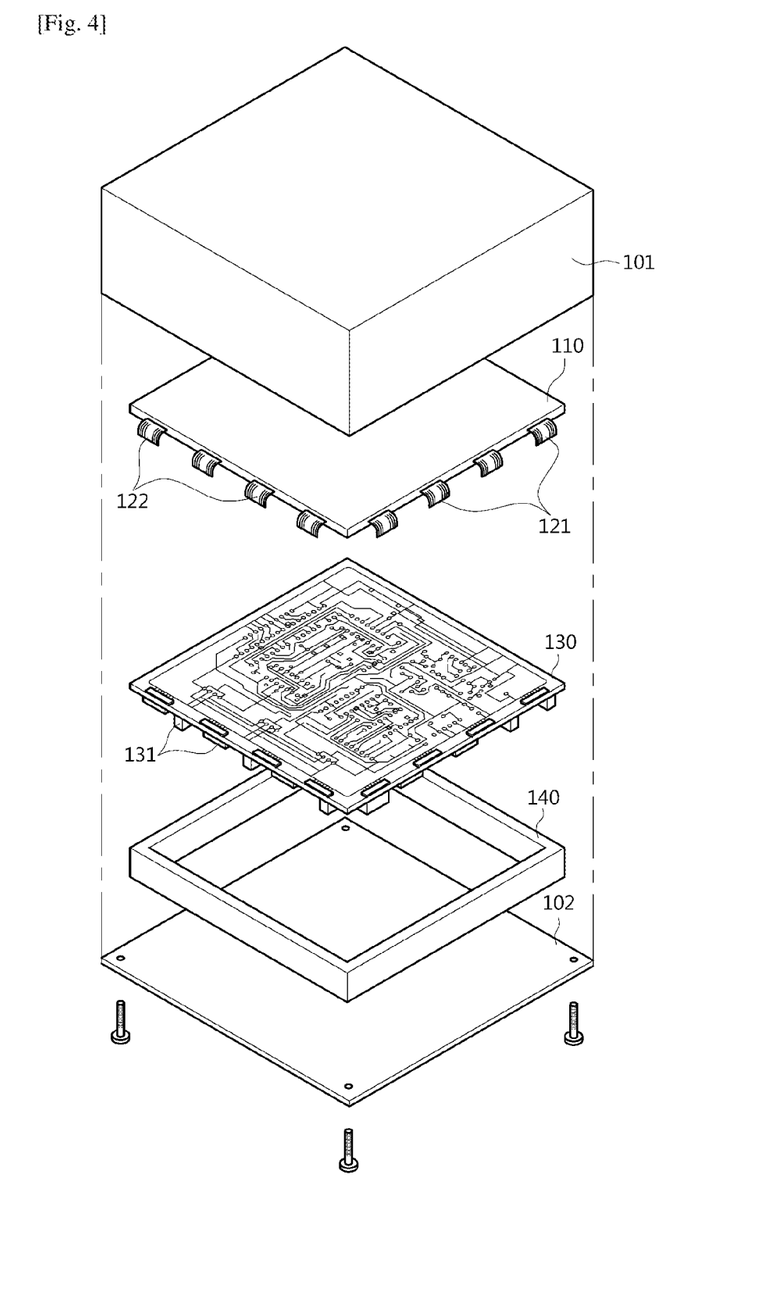
FIG. 4 is an exploded perspective view for explaining a layer structure of the x-ray detecting apparatus according to one embodiment.

FIG. 4 is an exploded perspective view for explaining a layer structure of the x-ray detecting apparatus according to one embodiment.

Referring to FIG. 4, the x-ray detecting apparatus 100 may include housings 101 and 102 forming an exterior appearances, a detecting panel 110 to detect x-rays, a circuit board 130 having circuits to drive the x-ray detecting apparatus 100, and a supporting member 140 to support the circuit board 130.

The housings 101 and 102 may include a upper housing 101 as well as a lower housing 102 provided in the shape that corresponds to the upper housing 101. As illustrated on FIG. 4, the upper housing 101 and the lower housing 102 may be coupled into each other by screws. However, the coupling method of the upper housing 101 and the lower housing 102 is not limited hereto.

The detecting panel 110, the circuit board 130, and the supporting member 140 may be sequentially accumulated at an inside the housings 101 and 102.

The detecting panel 110 is structured with a plurality number of pixels, and may be able to detect x-rays incident at the each pixel. Hereinafter, by referring to FIG. 5, schematic movements of the detecting panel 110 will be described.

Figure 5:
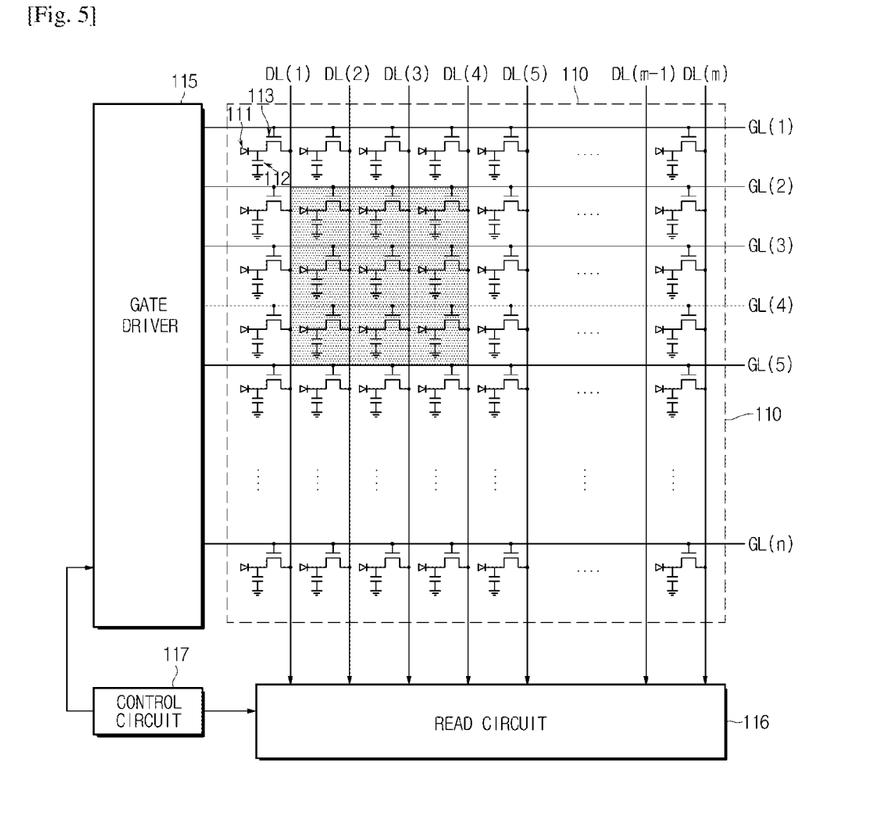
FIG. 5 is a controlled block diagram for explaining a detecting panel of the x-ray detecting apparatus according to one embodiment.

FIG. 5 is a controlled block diagram for explaining the detecting panel of the x-ray detecting apparatus according to one embodiment. As illustrated on FIG. 5, the detecting panel 110 is structured with the plurality number of pixels, and may be able to detect the x-rays that are radiated and also change the detected x-rays into electrical signals.

Also, the x-ray detecting apparatus 100 may further include a gate driver 115 to transmit ON/OFF signals with respect to read-outs to the detecting panel 110, a read circuit 116 to read-out the electrical signals that correspond to the strength of the x-rays from the detecting panel 110, and a control circuit 117 to control the x-ray detecting apparatus 100 in general.

As for the method of converting the x-rays detected from the detecting panel 110 into electrical signals, a direct conversion method and an indirect conversion method may be present.

With respect to the direction conversion method, when x-rays are incident at the detecting panel 110, a pair of electron and positive hole is temporarily formed at an inside a light-receiving device provided at the detecting panel 110, and the electron moves to a positive pole and the positive hole moves to a negative pole by the electricity applied at the both ends of the light-receiving device, and a read-out will be conducted on the flow of the electron or the positive hole at the read-out circuit board 130 as electrical signals. With respect to the direct conversion method, a photo-conductor, such as an a-Se (amorphous selenium), CdZnTe, Hgl2, or Pbl2, as the light-receiving device.

With respect to the indirect conversion method, a scintillator is further provided at the detecting panel 110, and when the incident x-rays are converted into visible rays by reacting with respect to the scintillator, the converted visible rays are detected by the light-receiving device to change the converted visible rays into electric signals. With respect to the indirect conversion method, a photodiode, such as a-Si (amorphous silicon) may be used as the light-receiving device, and as for the scintillator, a GADOX scintillator in the form of thin flim, micro pillar type, or a needle structure type CSI (T1) is used.

In one embodiment of the present invention, either the direct conversion method or the indirect conversion method may be used, but in the embodiment to be described hereinafter, the descriptions will be provided by applying the indirect conversion method.

As described above, the detecting panel 110 may be structured with the plurality of pixels. At this time, a photo diode 111 at which the charge corresponding to the strength of the x-rays incident is generated, a capacitor 112 to store the generated charge, and a switching device 113 to turn ON/OFF the flow of the charge stored at the capacitor 112 to flow through data line DL.

When the x-rays incident at the x-ray detecting apparatus 100 are converted into the visual rays by the scintillator and when the converted visual rays are reached at the photo diode 111, the photo diode 111 generates the amount of the charge corresponding to the strength of the visible rays. The generated charge is stored at the capacitor 112.

As one example f the switching device 113, a transistor may be used, and the switching device 113 may be implemented in the form of a TFT (Thin Film Transistor).

The switching devices 113 are connected by a same gate line GL, by row, and are connected by the same data line DL, by column. That is, as illustrated on FIG. 5, the m number of the switching devices 113 arranged on the same row are connected by the single gate line GL, and the n number of the switching devices 113 arranged on the same column are connected by the single data line DL.

When an ON signal is input at the switching device 113, the switching device is turned ON, and the charge stored at the capacitor 112 flows through the data line DL, and when an ON signal is not input, the OFF status of the switching device 113 is maintained so that the charge is accumulated at the capacitor 112.

When the gate driver 115 sequentially applies gate signals at the n number of the gate lines (the GL (1), the GL (2) . . . GL (n)), the m number of the switching devices 113 that are connected to the gate lines, which are applied with the gate signals, are turned ON, and the charge stored at the capacitors 112 of the corresponding pixel flows to the data lines DL through the switching devices 113. That is, the x-ray detecting apparatuses 100 and 110 may be able to obtain x-ray images by sequentially proceeding with line scans as the above.

Referring to FIG. 4 again, the detecting panel 110 may be provided while making contact with the first surface of the circuit board 130. As the above, when the detecting panel 110 is provided while making contact with the circuit board 130, the detecting panel 110 may be supported or fixed by the circuit board 130. For the above, the circuit board 130 may be provided in the shape that corresponds to the detecting panel 110.

Electronic components 131 needed to control the driving and controlling the x-ray detecting apparatus are installed at the second surface of the circuit board 130.

The circuit board 130, while having a base using a thin board manufactured by using insulation material such as epoxy resin or Bakelite resin, may be a printed circuit board formed by printing copper resist of blue color after forming wiring by using copper foil on top of the base, but is not limited hereto. For example, the circuit board 130 may be a wafer printed circuit board formed by performing rewiring process on the wafer itself.

At this time, the electronic components 131 may be a surface mounted components (SMC) that may be directly installed on the surface of the circuit board 113.

For example, the electronic components 131 may be the gate driver 115, the read circuit 116, or the control circuit 117 that are illustrated on FIG. 5. In particular, the gate driver 115 may be connected to the switching device of the detecting panel 110 through a first flexible PCB 121, and the read circuit 116 may be connected to the each pixel of the detecting panel 110 through a second flexible PCB 122.

At this time, the flexible PCBs 121 and 122 are boards using insulation panels that are flexible, and may be formed by using heat-resistant plastic film such as polyester PET or polyimide PI.

As the above, as the detecting panel 110 and the circuit board 113 are provided while bordering each other, the distance from the electronic components 131 to control the detecting panel 110 is further near with respect to the detecting panel 110, and therefore, the electrical noise of the circuit may be reduced.

Also, the supporting member 140 may be further included at inside the housings 101 and 102. A fixing member is provided in between the second surface of the circuit board 130 and the lower housing 102 to fix or support the circuit board 130.

The fixing member is provided along the borders of the circuit board 130 to form an accommodation groove at which the electronic components 131 protruded to an outside the circuit board 130 is accommodated.

As the above, since the circuit board 130 directly fixes and supports the detecting panel 110, the inside space of the x-ray detecting apparatus 100 may be used further efficiently. Hereinafter, by referring to FIG. 6, the layer structure of the x-ray detecting apparatus 100 will be described in detail.

Figure 6:
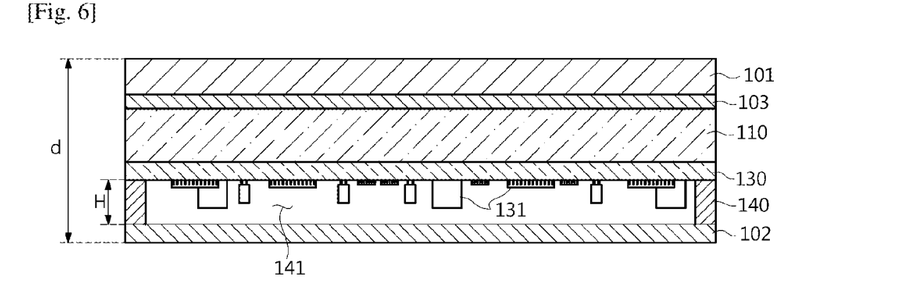
FIG. 6 is a cross-sectional view of the x-ray detecting apparatus for explaining the layer structure of the x-ray detecting apparatus according to one embodiment.

FIG. 6 is a cross-sectional view of the x-ray detecting apparatus for explaining the layer structure of the x-ray detecting apparatus according to one embodiment.

As illustrated on FIG. 6, the detecting panel 110, the circuit board 130, and the supporting member 140 may be sequentially accumulated in between the upper housing 101 and the lower housing 102.

A protective layer 103 may be provided in between the upper housing 101 and the detecting panel 110. The protective layer 103 protects the detecting panel 110 from an outside impact.

The protective layer 103 maybe formed by material having superiority over impacts and lower x-ray absorptions. For example, the protective layer 103 may be formed in carbon fiber.

At this time, the protective layer 103 may be provided while bonded at an upper surface of the detecting panel 110, but is not limited hereto. For example, the protective layer 103 may be provided while bonded at the upper housing 101.

The detecting panel 110 may be supported by the circuit board 130, and as the detecting panel 110 is bonded at the circuit board 130, the detecting panel 110 may be fixed at the circuit board 130. For example, the circuit board 130 and the detecting panel 110 may be bonded by using an adhesive/adhesive tape, or may be bonded by a pin connector.

As the above, without using a member for an additional fixing, since the detecting panel 110 is directly bonded at the circuit board 130, the weight of the x-ray detecting apparatus 100 may be minimized.

Also, since the coupling task to fix the circuit board 130 and the detecting panel 110 may be replaced by bonding, the x-ray detecting apparatus 100 may be manufactured further easily.

Also, since the circuit board 130 may be integrally formed in the shape that corresponds to the detecting panel 110, the electronic components 131 may be further efficiently designed and disposed.

The supporting member 140 supports the circuit board 130, and may fix the circuit board 130 while bonded with the circuit board 130. For example, the circuit board 130 and the detecting panel 110 may be bonded by using an adhesive/adhesive tape, or may be bonded by a pin connector.

As described above, since one surfaces of the upper sides of the circuit board 130 and the detecting panel 110 are bonded, the electronic components 131 are installed only at one surface of a lower side of the circuit board 130.

In particular, the electronic components 131 are accommodated at an accommodation unit 141 formed by the supporting member 140. As illustrated on FIG. 4 and FIG. 5, the supporting member 140 is provided in between a lower surface of the circuit board 130 and the lower housing 102 to support and fix the circuit board 130.

For the above, the supporting member 140 may be bonded at a lower surface of the circuit board 130 or at the lower housing 102.

As illustrated on FIG. 4 and FIG. 5, the accommodation unit 141 is formed at a predetermined height H by the supporting member 140. The electronic components 131 installed at the circuit board 130 is accommodated at the accommodation unit 140.

That is, as the detecting panel 110 and the circuit board 130 are directly coupled into each other, the height H of the accommodation unit 141, which is formed by the supporting member 140, from the total thickness d of the x-ray detecting panel 110 is relatively increased. Therefore, the electronic components 131 having higher height may be installed at the circuit board 130. Hereinafter, the structure of the supporting member will be described in detail.

Figure 7:
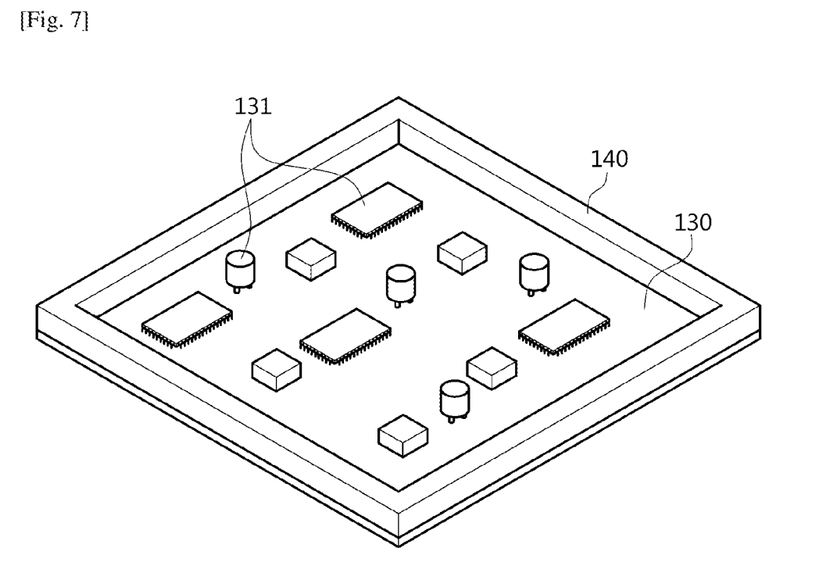
FIG. 7 is a drawing for explaining a supporting member of the x-ray detecting apparatus according to one embodiment.
Figure 8:
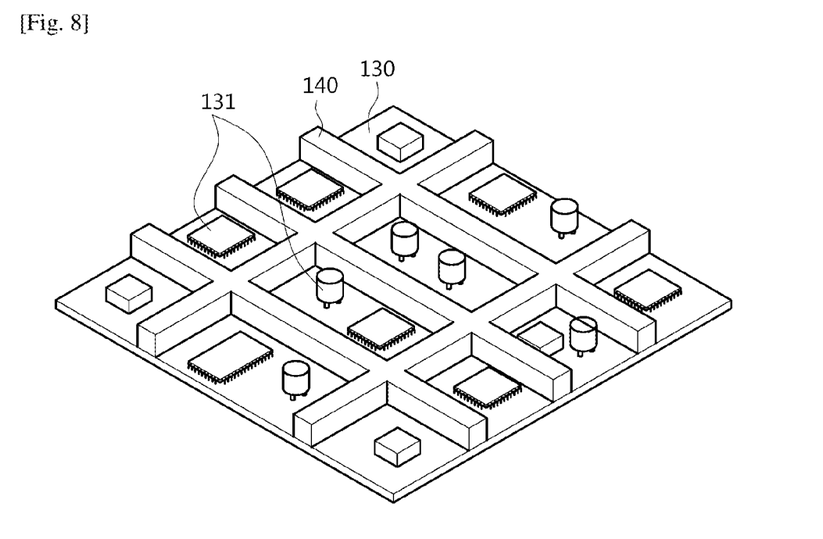
FIG. 8 is a drawing illustrating the supporting member of a lattice structure.
Figure 9:
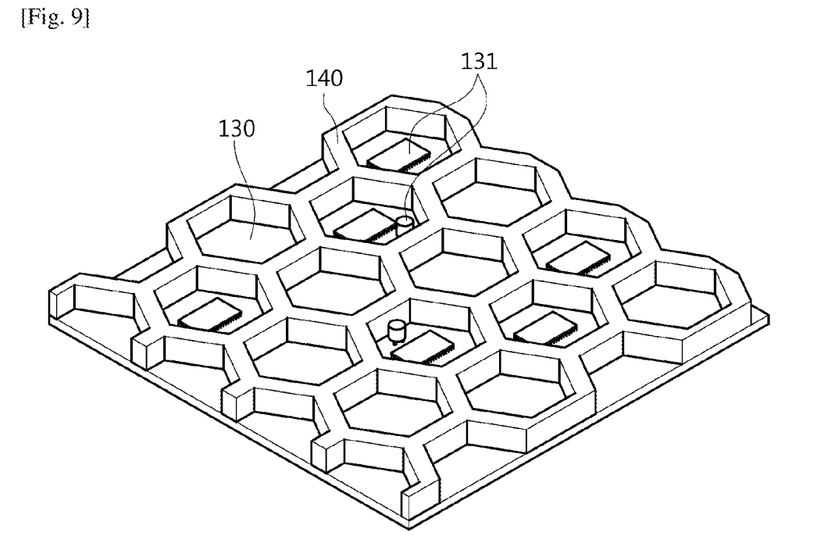
FIG. 9 is a drawing illustrating the supporting member of a honeycomb structure.

FIG. 7 is a drawing for explaining the supporting member of the x-ray detecting apparatus according to one embodiment, FIG. 8 is a drawing illustrating the supporting member of a lattice structure, and FIG. 9 is a drawing illustrating the supporting member of a honeycomb structure.

As illustrated on FIG. 7, the supporting member 140, while provided along the borders of on surface of a lower side of the circuit board 130, may be able to form the accommodation unit 141 to accommodate the electronic components 131 installed toward an outside the circuit board 130. At this time, the circuit board 130 may be designed so that the electronic components 131 are not installed at an area at which the circuit board 130 is bonded with the supporting member 140.

The supporting member 140 may fix the circuit board 130 at an inside the housings 101 and 102 while formed with material such as plastic, silicon, or rubber, and may be able to protect the electronic components 131 from outside impacts.

The supporting member 140 may be deformed in various shapes. In particular, the supporting member 140, as illustrated on FIG. 8, may be formed in a lattice structure having a certain distance with respect to each other. As the above, as the supporting member 140 is formed in the lattice structure, the circuit board 130 may be further firmly fixed, and the electronic components 131 installed at the circuit board 130 may be efficiently protected from outside impacts.

Also, as illustrated on FIG. 9, the supporting member 140 may be formed in a honeycomb structure. The honeycomb structure is referred to as a structure having regular hexagons each having a predetermined diameter are sequentially arranged, and as the supporting member 140 of the honeycomb structure is provided, the plurality of accommodation units 141 each having the shape of a regular hexagon is formed. As the above, as the supporting member 140 is formed in the honeycomb structure, the total area of the accommodation unit 141 at which the electronic components 131 are accommodated may be maximized.

Figure 10:
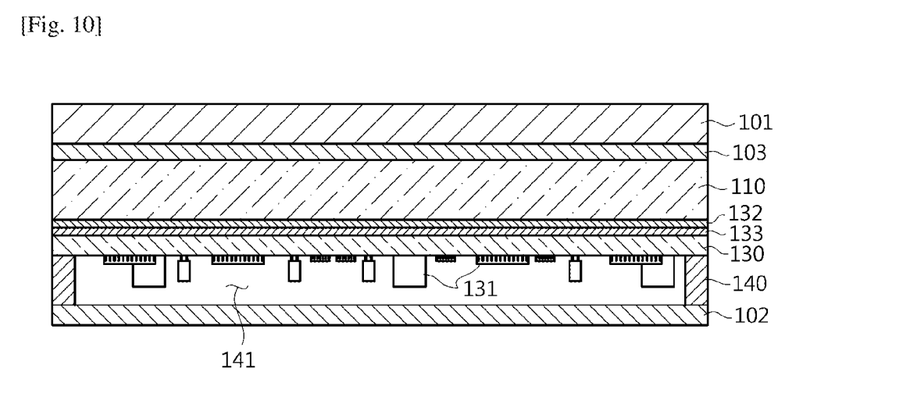
FIG. 10 is a cross-sectional view of an x-ray detecting apparatus for explaining a layer structure of an x-ray detecting apparatus according to another embodiment.

FIG. 10 is a cross-sectional view of the x-ray detecting apparatus for explaining a layer structure of an x-ray detecting apparatus according to another embodiment.

The x-ray detecting apparatus 100 according to another embodiment may further include a buffer unit 132 and a shielding layer 133.

The buffer unit 132 is provided in between the detecting panel 110 and the circuit board 130 to protect the circuit board 130. In general, since the x-ray detecting apparatus 100 is manufactured with the thickness of less than about 15 mn, the circuit board 130 may be damaged by outside impact or deformation. For the above, the buffer unit 132 protects the circuit board 130 by buffering the impact delivered from the detecting panel 110.

The shielding layer 133 may be able to shield x-rays by absorbing the x-rays. In particular, the shielding layer 133 is provided in between the detecting panel 110 and the circuit board 130 to protect the circuit board 130 nd the electronic components 131 by absorbing the x-rays incident after penetrating the detecting panel 110.

Also, since the shielding layer 133 prevents incidence x-rays, which are diffusedly reflected after penetrating the detecting panel 110, from incident again at the detecting panel 110, further clearer and precise x-ray images may be obtained.

For example, the shielding layer 133 is provided with film having material such as copper, which is provided with higher absorption rate of x-rays, and may be bonded at one surface of an upper side of the circuit board 130.

Meanwhile, on FIG. 8, the shielding layer 133 is illustrated to be provided under the buffer unit 132, but the positions of the shielding layer 133 and the buffer unit 132 may be switched with respect to each other.

The invention claimed is:

1. An x-ray detecting apparatus, comprising:
a housing;
a detecting panel provided an inside the housing and configured to detect x-rays on a detecting surface; and
a circuit board having:
a first surface, which makes a direct contact with a proximate surface of the detecting panel, is bonded to the proximate surface, and comprises electrical connections disposed thereon facing the proximate surface, to make an electrical contact with the detecting panel, wherein the proximate surface is opposite to the detecting surface, and
a second surface provided with at least one electronic component installed thereto,
wherein the first surface of the circuit board structurally supports the proximate surface of the detecting panel.

2. The x-ray detecting apparatus of claim 1, further comprising:
a supporting member provided on the second surface of the circuit board to support the circuit board.

3. The x-ray detecting apparatus of claim 2, wherein the supporting member comprises at least one accommodation unit at which a device installed at the circuit board is accommodated.

4. The x-ray detecting apparatus of claim 2, wherein the supporting member is formed along borders of the circuit board.

5. The x-ray detecting apparatus of claim 2, wherein the supporting member is formed in a lattice structure.

6. The x-ray detecting apparatus of claim 2, wherein the supporting member is formed in a honeycomb structure.

7. The x-ray detecting apparatus of claim 1, wherein the circuit board and the detecting panel are bonded by an adhesive.

8. The x-ray detecting apparatus of claim 1, wherein the circuit board and the detecting panel are bonded by a pin connector.

9. The x-ray detecting apparatus of claim 2, wherein the circuit board and the supporting member are bonded to each other.

10. The x-ray detecting apparatus of claim 1, further comprising:
a protective layer provided between the detecting panel and the housing to absorb an outside impact.

11. The x-ray detecting apparatus of claim 1, wherein the first surface of the circuit board supports an entirety of the proximate surface of the detecting panel.

12. An x-ray detecting apparatus, comprising:
a detecting panel configured to detect x-rays on a detecting surface;
a circuit board having:

a first surface, which makes a direct contact with a proximate surface of the detecting panel, is bonded to the proximate surface, and comprises electrical connections disposed thereon facing the proximate surface, to make an electrical contact with the detecting panel, wherein the proximate surface is opposite to the detecting surface, and a second surface provided with electronic components installed thereto; and a supporting member provided at the second surface of the circuit board to protect the electronic components from outside impact, wherein the first surface of the circuit board structurally supports the proximate surface of the detecting panel.

13. The x-ray detecting apparatus of claim 12, wherein the circuit board and the detecting panel are bonded by an adhesive.

14. The x-ray detecting apparatus of claim 12, wherein the circuit board is bonded to the supporting member.

15. The x-ray detecting apparatus of claim 12, wherein the supporting member comprises an accommodation unit to accommodate at least one electronic component, among the electronic components.

16. The x-ray detecting apparatus of claim 15, wherein the supporting member is provided along borders of the circuit board, and the accommodation unit is formed at a center portion of the supporting member.

17. The x-ray detecting apparatus of claim 15, wherein the accommodation unit is formed in a lattice structure.

18. The x-ray detecting apparatus of claim 15, wherein the accommodation unit is formed in a honeycomb structure.

19. The x-ray detecting apparatus of claim 12, wherein the circuit board and the detecting panel are bonded by a pin connector.

* * * * *